(12) United States Patent
Shu

(10) Patent No.: US 6,818,017 B1
(45) Date of Patent: Nov. 16, 2004

(54) HIGH GAIN WIDE RANGE ACCOMMODATING INTRAOCULAR LENS FOR IMPLANT INTO THE CAPSULAR BAG

(76) Inventor: Stephen Shu, 8 Viewpointe Pl., Laguna Niguel, CA (US) 92677

(*) Notice: Subject to any disclaimer, the term of this patent is extended or adjusted under 35 U.S.C. 154(b) by 0 days.

(21) Appl. No.: 09/788,041

(22) Filed: Feb. 15, 2001

(51) Int. Cl.$^7$ .................................................. A61F 2/16
(52) U.S. Cl. .................... 623/6.11; 623/6.32; 623/6.34; 623/6.37
(58) Field of Search ............................... 623/6.11, 6.13, 623/6.15, 6.22, 6.24, 6.27, 6.32, 6.34, 6.37, 6.38, 6.43

(56) References Cited

U.S. PATENT DOCUMENTS

| | | | | |
|---|---|---|---|---|
| 5,152,788 A | * | 10/1992 | Isaacson et al. | 623/6.13 |
| 5,489,302 A | * | 2/1996 | Skottun | 623/6.13 |
| 5,964,802 A | * | 10/1999 | Anello et al. | 439/76.1 |
| 6,464,725 B2 | * | 10/2002 | Skottun | 623/6.34 |
| 2002/0002404 A1 | * | 1/2002 | Sarfarazi | 623/6.34 |

FOREIGN PATENT DOCUMENTS

| | | | |
|---|---|---|---|
| JP | 02126847 A | * | 5/1990 |
| WO | WO 00/66037 | * | 9/2000 |

* cited by examiner

*Primary Examiner*—David J. Isabella
*Assistant Examiner*—Kamrin Landrem
(74) *Attorney, Agent, or Firm*—Leonard Tachner

(57) ABSTRACT

A high gain lens system for implant into the capsular bag after removal of the natural crystalline lens. A preferred embodiment of the invention comprises a combination of a positive or convex lens and a negative or concave lens. These two lenses are spaced from one another and their relative spacing and respective focal lengths determine their combined focal length. When the lens system is inserted into the capsular bag, two opposed haptic flanges on each side, extend toward the inner radial edge of the bag adjacent the ciliary muscles. When the muscles contract, the bag is stretched thereby compressing the haptic flanges together or at least toward one another. This action cause the two lenses to separate further from each other and the increased spacing between the positive and negative lenses shortens the focal length to permit focusing of objects at near distances. On the other hand, when the muscles relax, the bag relaxes also, the haptic flanges separate and the lenses come closer together. The reduced spacing between the positive and negative lenses, increases the focal length to permit focusing of objects at far distances.

7 Claims, 6 Drawing Sheets

HIGH GAIN WIDE RANGE ACCOMMODATING INTRAOCULAR LENS FOR IMPLANT INTO THE CAPSULAR BAG

BACKGROUND OF THE INVENTION

1. Field of the Invention

The present invention relates generally to intraocular lens implants and more specifically to a high gain implantable intraocular lens which utilizes a dual lens device to reduce capsular bag action to achieve focal point accommodation with minimal stress on ciliary muscles.

2. Background Art

The most relevant prior art appears to be disclosed in U.S. Pat. No. 5,674,282 issued on Oct. 7, 1997 to Cumming. This disclosure also relates to an accommodating intraocular lens designed to be implanted in the human eye capsular bag after the natural crystalline lens has been surgically removed such as during cataract surgery. Accommodation is the muscle-controlled change in focal point of the eye lens such as for viewing an object near the eye after initially viewing a distant object.

The lens disclosed in the Cumming patent is a relatively simple convex lens and accommodation requires movement of the lens toward and away from the retina of the eye. Unfortunately, because the gain of a simple convex lens is low, the distance the lens must be actually moved within the eye to achieve a large focal length change, is relatively large. Requiring a large distance for lens movement means that achieving accommodation for near vision is difficult at best and may ultimately become impossible when the ciliary muscles become too weak or too tired to achieve the necessary lens movement.

It would be highly advantageous if an implantable intraocular lens for ciliary muscle accommodation control, could be designed to permit large focal point variation and range of accommodation with less muscle strain. In other words, a higher gain controllable lens, which provides needed accommodation with less movement and less muscle exertion, would be an extremely desirable improvement. One prior art attempt at an implantable complex lens device to provide muscle control accommodation is disclosed in U.S. Pat. No. 5,275,623 to Sarforazi wherein two spaced convex lenses have their spacing altered by muscle control of the capsular bag. However, a dual convex lens system still requires a substantial movement to accommodate large focal point variation.

SUMMARY OF THE INVENTION

The present invention comprises a high gain lens system for implant into the capsular bag after removal of the natural crystalline lens, such as a result of cataract surgery. While the invention herein has certain characteristics in common with the prior art such as the aforementioned patents to Cumming and Sarforazi, its uniqueness resides in the achievement of a higher optical gain and greater range of accommodation which provides full focal length accommodation with less muscle exertion. A preferred embodiment of the invention comprises a combination of a positive or convex lens and a negative or concave lens. These two lenses are spaced from one another and their relative spacing and respective focal lengths determine their combined focal length. The two lenses are joined along their perimeters through a common, interface which may be either integral to or attached to the respective lenses. In the preferred embodiment, the interface is formed as a narrow, flexible joint which acts an annular pivot for controlling the spacing between the lenses. The interface extends radially from this joint along two substantially parallel planes around opposing portions of the lens structure forming a scissor-like pair of closely spaced haptic flanges on each of two opposed sides of the lenses.

When the lens system of the preferred embodiment is inserted into the capsular bag, the two opposed haptic flanges on each side, extend toward the inner radial edge of the bag adjacent the ciliary muscles. When the muscles contract, the bag is stretched thereby compressing the haptic flanges together or at least toward one another. This action cause the two lenses to separate further from each other and the increased spacing between the positive and negative lenses shortens the focal length to permit focusing of objects at near distances. On the other hand, when the muscles relax, the bag relaxes also, the haptic flanges separate and the lenses come closer together. The reduced spacing between the positive and negative lenses, increases the focal length to permit focusing of objects at far distances. Thus, the preferred embodiment permits muscle control of the focal length of the lens system. Moreover, it will be seen hereinafter that the amount of movement of the lenses relative to one another to achieve a given change in focal length is relatively small because the optical gain is high. Therefore, the invention herein constitutes a significant advance over the prior art by providing a practical lens system that permits easier and greater extent of accommodation using ciliary muscles attached to the capsular bag. A second embodiment of the invention employs the same two lenses of the first embodiment, but with a different spacing control implementation based on the same pivoting scissor technique. A third embodiment employs an enclosed ring forming a unitary pressure chamber where increased pressure separates the two lenses.

An important benefit of the lens system of all of the disclosed embodiments is the large range of focal lengths that result. Such a large range assures compensation for changing lens characteristics due to aging or infirmities such as nearsightedness.

OBJECTS OF THE INVENTION

It is therefore a principal object of the present invention to provide an implantable intraocular high gain lens having a large range adjustable focal length which can be controlled by eye muscles.

It is another object of the present invention to provide a focal length adjustable implantable intraocular lens which has a higher gain and larger range than such lenses of the prior art.

It is still another object of the invention to provide a complex adjustable lens system for implanting into the capsular bag of the human eye, the lens system having a positive lens and a negative lens and yielding a high optical gain based upon the relative spacing of the two lenses.

It is yet another object of the invention to provide a high gain, large range, accommodating implantable lens system configured for aligning a positive lens and a negative lens as they are moved axially relative to one another to alter their combined focal point.

It is yet another object of the invention to provide an implantable, adjustable lens system the focal length of which may be varied over a sufficiently large range to accommodate near and far vision requirements even with changing characteristics over the entire adult life of a user.

It is yet another object of the invention to provide an implantable adjustable lens system wherein a muscle-activated scissor-like operation assures continuous alignment of the lenses of the system regardless of the application of unbalanced forces.

BRIEF DESCRIPTION OF THE DRAWINGS

The aforementioned objects and advantages of the present invention, as well as additional objects and advantages thereof, will be more fully understood hereinafter as a result of a detailed description of a preferred embodiment when taken in conjunction with the following drawings in which:

FIG. 5, comprising

FIG. 7, comprising

DETAILED DESCRIPTION OF A PREFERRED EMBODIMENT

Figure 1:
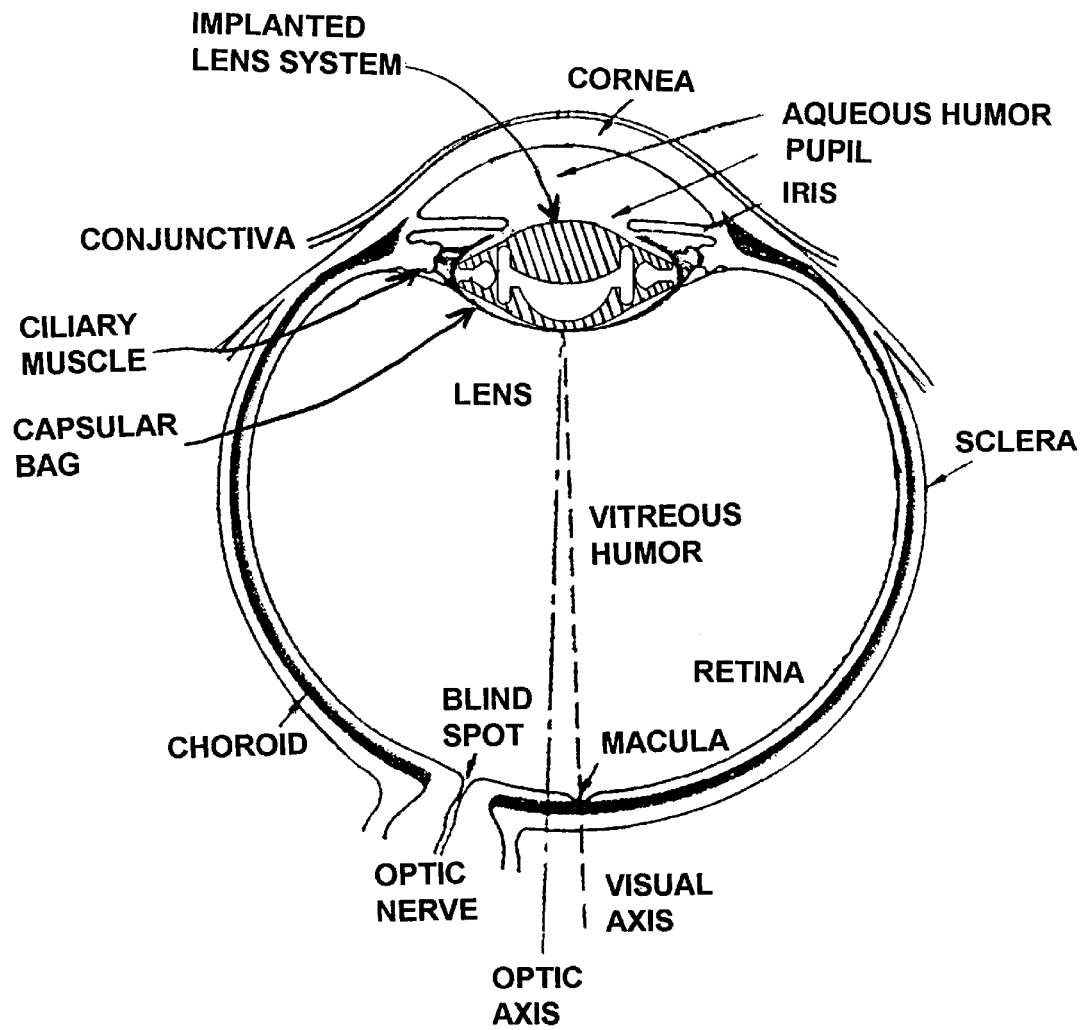
FIG. 1 is a cross-sectional view of a human eye shown with the natural crystalline lens removed and replaced with a preferred embodiment of the invention.

Referring to the accompanying figures, and initially FIG. 1, it will be seen that in a human eye immediately behind the cornea, the aqueous humor and the pupil, there is a capsular bag attached to ciliary muscles. In a normal human eye, the capsular bag is filled with a crystalline lens which the bag fully encloses. However, in FIG. 1, it is assumed that the eye has undergone surgery to cut through a portion of the capsular bag and to remove the entire crystalline lens. A technical description of this type of eye surgery, which is commonly done to remedy the condition know as "cataracts", is provided in the aforementioned Cumming U.S. Pat. No. 5,674,282 which patent disclosure is incorporated herein by reference. It is further assumed that a lens system according to a preferred embodiment of the invention, has been installed into the capsular bag after the natural lens has been removed. It is further assumed that a portion of the capsular bag facing the cornea and immediately behind the iris, may have been permanently removed as part of the surgical process to remove the natural crystalline lens. However, the operation of the inventive lens system will not be significantly affected by such removal of a portion of the capsular bag as long as that portion of the bag to which the ciliary muscles are attached, remains intact.

It will be seen in FIG. 1, that the inventive lens system substantially fills the capsular bag extending radially to the inner radial surface of the bag and extending axially virtually to the anterior and posterior limits of the bag's inner surface.

Figure 2:
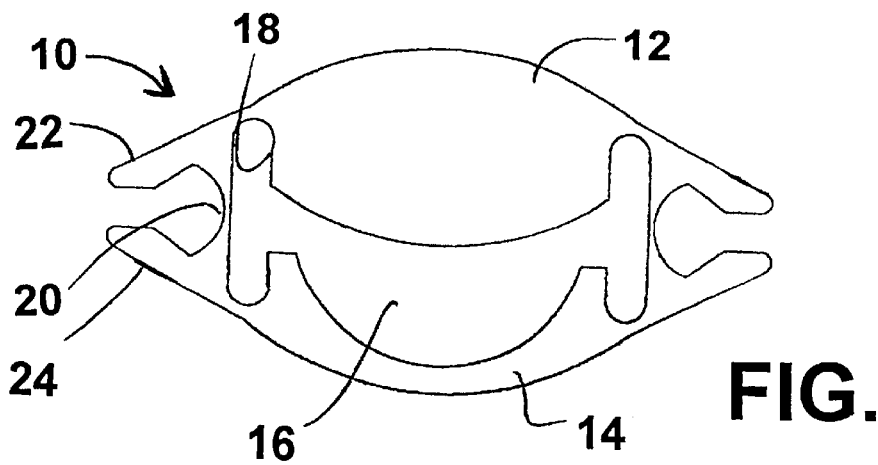
FIG. 2 is a cross-sectional view of the preferred embodiment shown in a near vision configuration.
Figure 3:
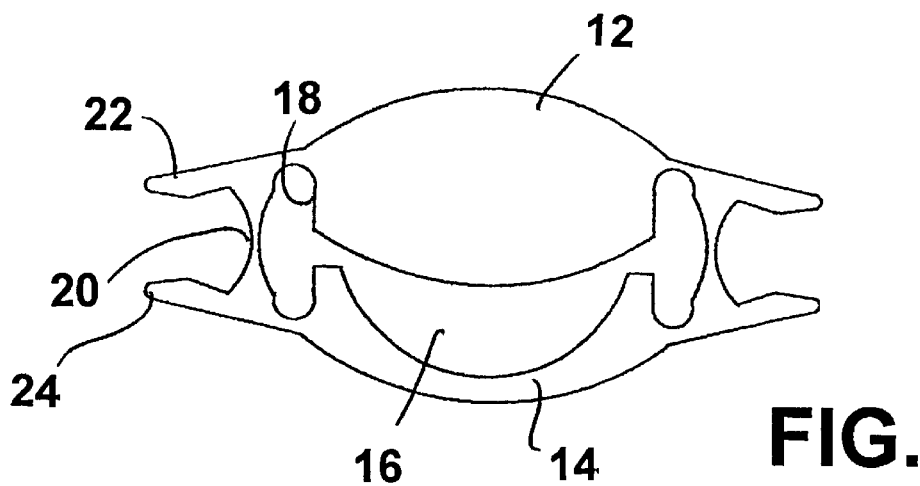
FIG. 3 is a cross-sectional view of the preferred embodiment shown in a far vision configuration.
Figure 4:
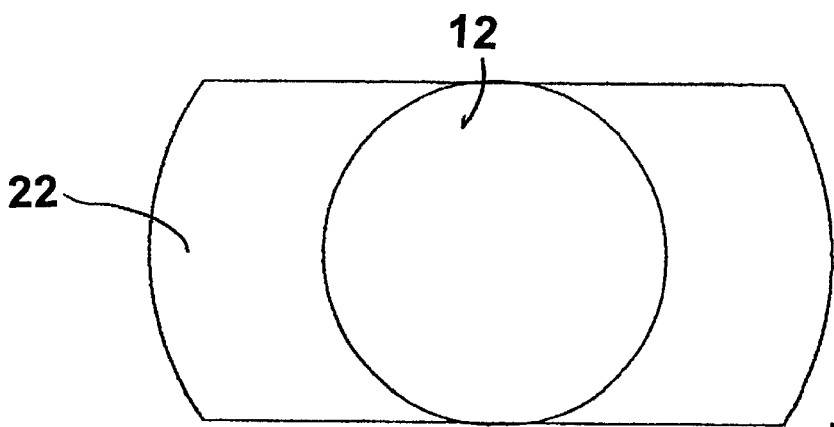
FIG. 4 is a top view of the preferred embodiment.

Referring now to FIGS. 2–4, it will be seen that a lens system 10 comprises a positive or convex lens 12 and a negative or concave lens 14. The lenses 12 and 14 are separated by a chamber 16 which terminates in an annular gap 18. The two lenses are connected along their radial edge at fulcrum 20 which radially separates lenses 12 and 14 from a pair of haptics 22 and 24 on each of the said lens system 10, the haptics providing a lever effect on the lenses much like a pair of scissors or pliers.

In operation, haptics 22 and 24 are either compressed together or relaxed apart. The lenses 12 and 14 do just the opposite of the haptics. Specifically, when the haptics 22 and 24 are compressed together by the ciliary muscles and capsular bag, the lenses separate, thereby increasing the width of chamber 16 to the extent shown in FIG. 2. In this configuration, the combined focal length of the two lenses 12 and 14, is shortened which is required for near distance viewing. On the other hand, when the haptics 22 and 24 are relaxed apart by relaxation of the ciliary muscles and capsular bag, the lenses come closer together, thereby decreasing the width of chamber 16 to the extent shown in FIG. 3. In this configuration, the combined focal length of the two lenses 12 and 14, is lengthened which is required for far distance viewing.

Figure 5A:
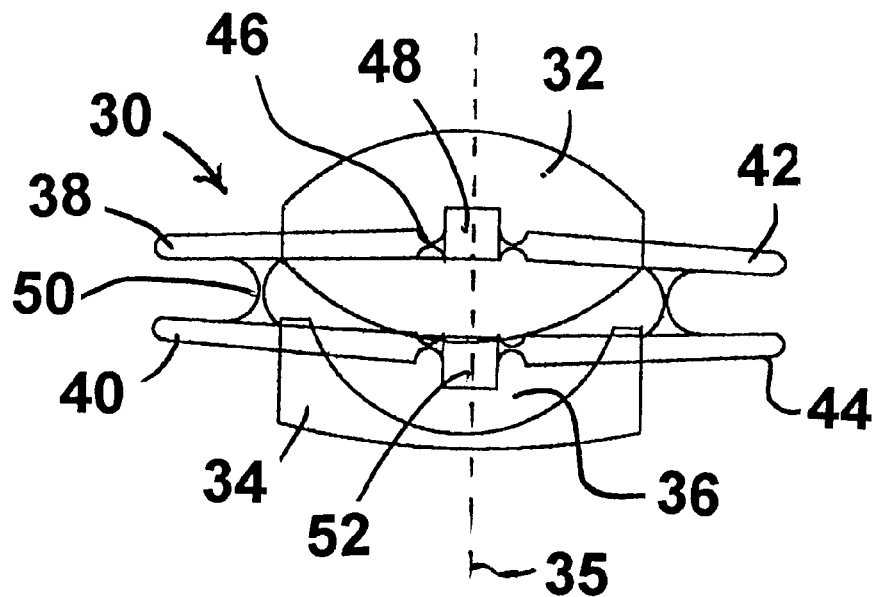
FIGS. 5a and 5b, is a side view of alternative embodiments shown in relaxed and extended positions.
Figure 5B:
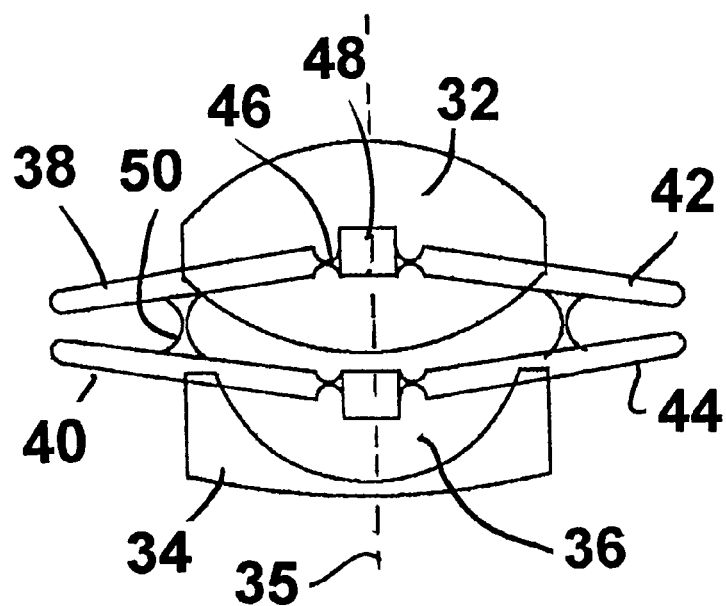
Figure 6:
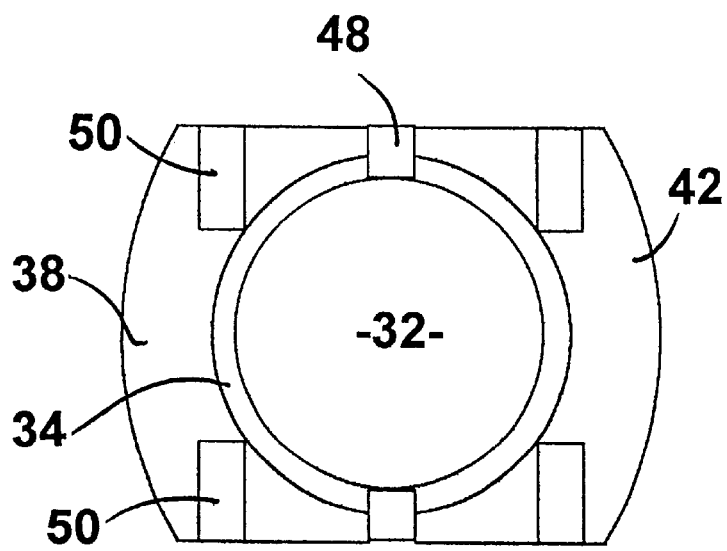
FIG. 6 is a top view of the alternative embodiment.

A second embodiment of the invention illustrated in FIGS. 5 and 6, operates in essentially the same way as the first embodiment of FIGS. 2 through 4. The principal difference resides in the mechanism to control the distance between the lenses. Specifically, a lens system 30 comprises a positive lens 32 and a negative lens 34 separated by a chamber 36. The spacing between the lenses 32 and 34 is controlled by haptics 38, 40, 42 and 44. Each such haptic is attached to a lens by means of a flex interface (i.e., interface 48 for lens 32 and interface 52 for lens 34). Each flex interface provides a bend point such as point 46. A fulcrum 50 on each side of lenses 32 and 34 provides a pivot for compression of haptics 38, 40, 42 and 44 which increases the distance between lenses 32 and 34 analogous to FIG. 2 for the first embodiment, or permits a relaxation of the haptics, which decreases the distance between the lenses analogous to FIG. 3 of the first embodiment.

Figure 8:
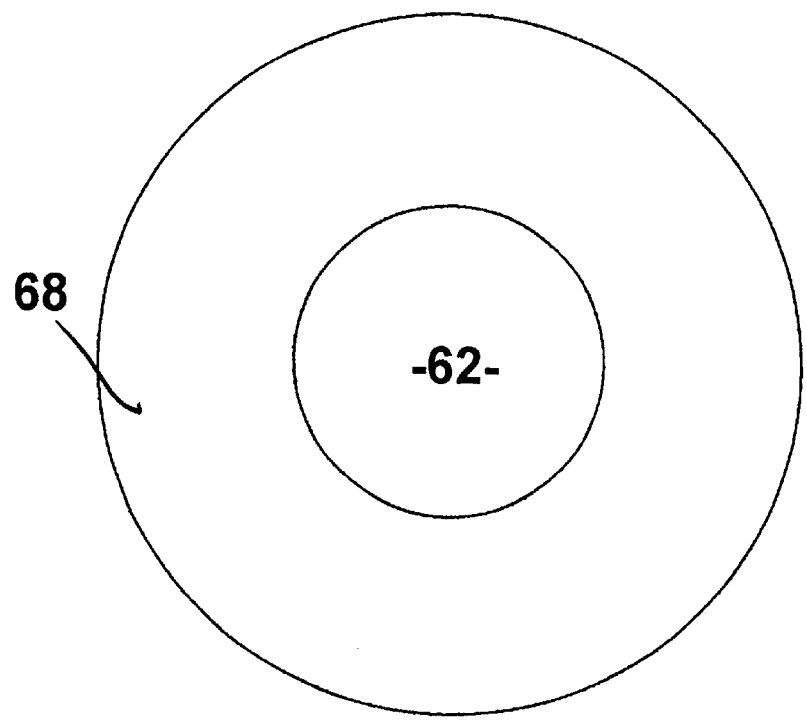
FIG. 8 is a top view of the embodiment of FIG. 7.
Figure 7A:
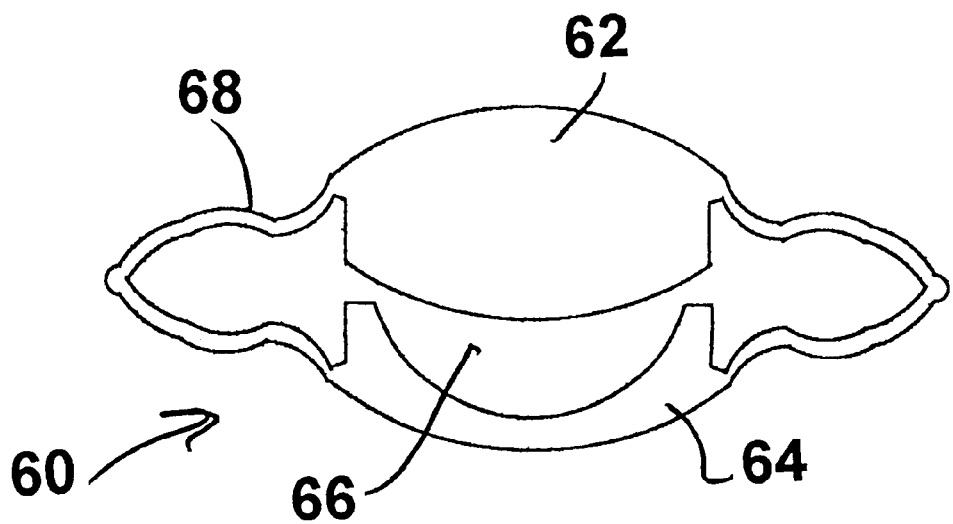
FIGS. 7a and 7b, is a side view of another alternative embodiment shown in relaxed and extended positions.
Figure 7B:
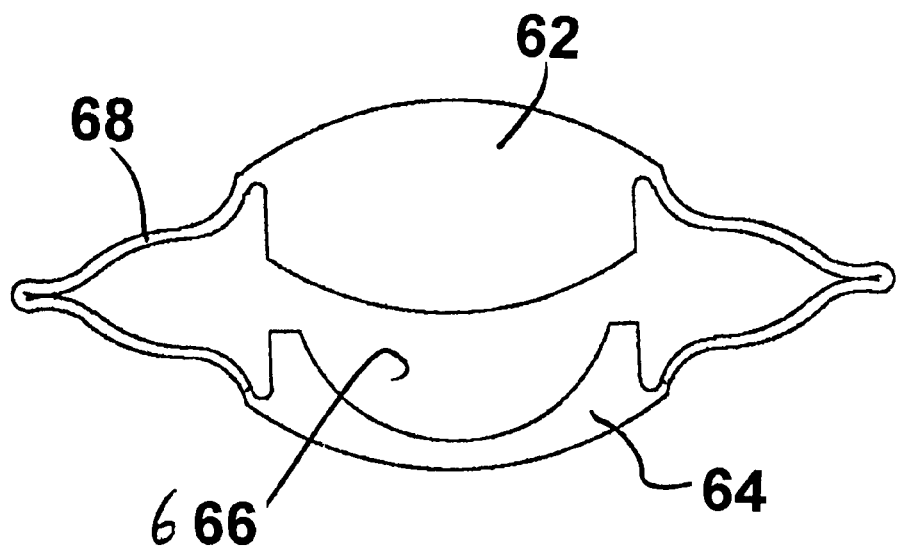

In another embodiment shown in FIGS. 7 and 8, a lens system 60 has a positive lens 62 and a negative lens 64 separated by a chamber 66. Chamber 66 may be filled with a gas (i.e., air) or a clear liquid (i.e., saline, water, et cetera). This embodiment is much like the embodiment of FIGS. 1–4, but ring 68 is fully enclosed to form a unitary chamber which permits internal chamber pressure to play a role in controlling separation between lenses 62 and 64. As shown in FIG. 7b, when the ring 68 is compressed (i.e., by the capsular bag) the increased pressure pushes lenses 62 and 64 further apart. Lenses 62 and 64 can be made of a high index material such as sapphire which has a refractive index of 1.77 which results in a smaller and thinner assembly.

Figure 9:
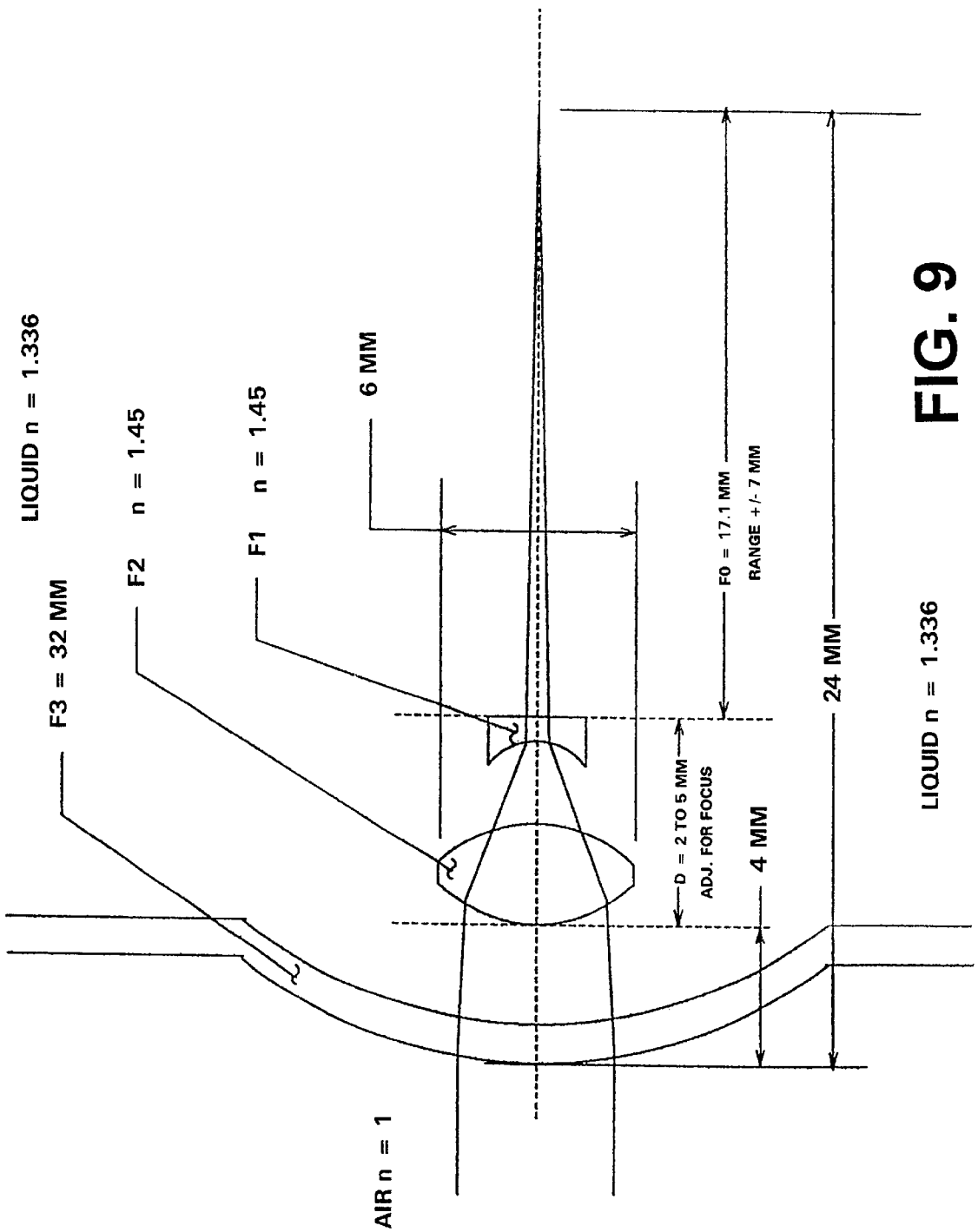
FIG. 9 is a ray diagram of the lens system of the invention.

A key feature of the present invention is the high optical gain and large accommodation range of a lens system having spaced positive and negative lenses. As used herein, the term optical gain is the ratio of focal length change for the combined lenses to the change in distance between lenses to achieve that focal length change. FIG. 9 and Table 1 show what the gain and range are for the lens system of the present invention. FIG. 9 helps to define the terms used in Table 1. Table 1 specifies the optical gain and large range for a number of different positive and negative lenses. Thus for example, for $F_1=-9$ mm and $F_2=+9$ mm with D between 2.4 mm and 3.3 mm, the gain is between 14.7 and 7.7. This means that for a change in $F_O$ of 1 mm, the distance D has to change only about 0.07 to 0.13 mm. In another example, for $F_1=-7$ and $F_2=+7$ with D between 1.5 mm and 2.2 mm, the gain is between 23 and 10. This means that for a change in $F_0$ of 1 mm, the distance D has to change only about 0.04 mm to 0.1 mm.

In general terms, the combined focal length $F_0$ of the two lenses $F_1$ for the negative lens and $F_2$ for the positive lens is determined by the formula:

$$F_0 = [F_2 \cdot (D - F_1)] / [D - (F_1 + F_2)] \quad (1)$$

where D=the distance between the two lenses. Moreover, the gain=$\Delta F_0/\Delta D$. From Table 1 it can be seen that for $F_1$ between −7 mm and −11 mm and $F_2$ between +7 and +12, the gain varies between about 6 and 23 for lens spacing between about 1.5 and 5 mm. Thus, for those values of $F_1$ and $F_2$, a change in the distance between the lenses will produce between 6 and 23 times that change in the focal length of the combined lens system. It can be seen in equation (1) that the reason for this large gain in a lens system having positive and negative lenses is that $F_1$ and $F_2$ are of opposite polarity thereby increasing the impact of D in the denominator on the value of $F_0$.

Thus, because the burden on the ciliary muscles to move the lenses relative to one another is reduced, the change in $F_0$ can be more readily accomplished over a wider range in the present invention then in the most relevant prior art implantable lens systems. Moreover, the unique structure of each of the disclosed embodiments, assures that the respective lenses always remain axially aligned with one another to assure excellent optical performance over a period of decades. Thus, for example in FIGS. 5a and 5b, it is seen that the lenses 32 and 34 remain axially centered and aligned along centerline 35 whether separated or not. Moreover, because of the unique scissor-like operation, even unbalanced activation forces will not displace either lens from that centerline.

TABLE 1

| F1 | F2 | D | F0 | GAIN | F1 | F2 | D | F0 | GAIN | F1 | F2 | D | F0 | GAIN | F1 | F2 | D | F0 | GAIN |
|---|---|---|---|---|---|---|---|---|---|---|---|---|---|---|---|---|---|---|---|
| −7.0 | 7.0 | 1.50 | 25.7 | 23.3 | −7.0 | 8.0 | 2.50 | 25.7 | 23.3 | −7.0 | 9.0 | 3.50 | 25.7 | 23.3 | −7.0 | 10.0 | 4.50 | 25.7 | 23.3 |
| −7.0 | 7.0 | 1.60 | 23.6 | 20.4 | −7.0 | 8.0 | 2.60 | 23.6 | 20.4 | −7.0 | 9.0 | 3.60 | 23.6 | 20.4 | −7.0 | 10.0 | 4.60 | 23.6 | 20.4 |
| −7.0 | 7.0 | 1.70 | 21.8 | 18.0 | −7.0 | 8.0 | 2.70 | 21.8 | 18.0 | −7.0 | 9.0 | 3.70 | 21.8 | 18.0 | −7.0 | 10.0 | 4.70 | 21.8 | 18.0 |
| −7.0 | 7.0 | 1.80 | 20.2 | 16.0 | −7.0 | 8.0 | 2.80 | 20.2 | 16.0 | −7.0 | 9.0 | 3.80 | 20.2 | 16.0 | −7.0 | 10.0 | 4.80 | 20.2 | 16.0 |
| −7.0 | 7.0 | 1.90 | 18.8 | 14.3 | −7.0 | 8.0 | 2.90 | 18.8 | 14.3 | −7.0 | 9.0 | 3.90 | 18.8 | 14.3 | −7.0 | 10.0 | 4.90 | 18.8 | 14.3 |
| −7.0 | 7.0 | 2.00 | 17.5 | 12.9 | −7.0 | 8.0 | 3.00 | 17.5 | 12.9 | −7.0 | 9.0 | 4.00 | 17.5 | 12.9 | −7.0 | 10.0 | 5.00 | 17.5 | 12.9 |
| −7.0 | 7.0 | 2.10 | 16.8 | 11.7 | −7.0 | 8.0 | 3.10 | 16.8 | 11.7 | −7.0 | 9.0 | 4.10 | 16.8 | 11.7 | −7.0 | 10.0 | 5.10 | 16.8 | 11.7 |
| −7.0 | 7.0 | 2.20 | 15.3 | 10.6 | −7.0 | 8.0 | 3.20 | 15.3 | 10.6 | −7.0 | 9.0 | 4.20 | 15.3 | 10.6 | −7.0 | 10.0 | 5.20 | 15.3 | 10.6 |
| −9.0 | 9.0 | 2.40 | 24.8 | 14.7 | −9.0 | 8.0 | 3.40 | 24.8 | 14.7 | −9.0 | 11.0 | 4.40 | 24.8 | 14.7 | −9.0 | 12.0 | 5.40 | 24.8 | 14.7 |
| −9.0 | 9.0 | 2.50 | 23.4 | 13.5 | −9.0 | 8.0 | 3.50 | 23.4 | 13.5 | −9.0 | 11.0 | 4.50 | 23.4 | 13.5 | −9.0 | 12.0 | 5.50 | 23.4 | 13.5 |
| −9.0 | 9.0 | 2.60 | 22.2 | 12.5 | −9.0 | 10.0 | 3.60 | 22.2 | 12.5 | −9.0 | 11.0 | 4.60 | 22.2 | 12.5 | −9.0 | 12.0 | 5.60 | 22.2 | 12.5 |
| −9.0 | 9.0 | 2.70 | 21.0 | 11.5 | −9.0 | 10.0 | 3.70 | 21.0 | 11.5 | −9.0 | 11.0 | 4.70 | 21.0 | 11.5 | −9.0 | 12.0 | 5.70 | 21.0 | 11.5 |
| −9.0 | 9.0 | 2.80 | 19.9 | 10.7 | −9.0 | 10.0 | 3.80 | 19.9 | 10.7 | −9.0 | 11.0 | 4.80 | 19.9 | 10.7 | −9.0 | 12.0 | 5.80 | 19.9 | 10.7 |
| −9.0 | 9.0 | 2.90 | 18.9 | 10.0 | −9.0 | 10.0 | 3.90 | 18.9 | 10.0 | −9.0 | 11.0 | 4.90 | 18.9 | 10.0 | −9.0 | 12.0 | 5.90 | 18.9 | 10.0 |
| −9.0 | 9.0 | 3.00 | 18.0 | 9.3 | −9.0 | 10.0 | 4.00 | 18.0 | 9.3 | −9.0 | 11.0 | 5.00 | 18.0 | 9.3 | −9.0 | 12.0 | 6.00 | 18.0 | 9.3 |
| −9.0 | 9.0 | 3.10 | 17.1 | 8.7 | −9.0 | 10.0 | 4.10 | 17.1 | 8.7 | −9.0 | 11.0 | 5.10 | 17.1 | 8.7 | −9.0 | 12.0 | 6.10 | 17.1 | 8.7 |
| −9.0 | 9.0 | 3.20 | 16.3 | 8.2 | −9.0 | 10.0 | 4.20 | 16.3 | 8.2 | −9.0 | 11.0 | 5.20 | 16.3 | 8.2 | −9.0 | 12.0 | 6.20 | 16.3 | 8.2 |
| −9.0 | 9.0 | 3.30 | 15.5 | 7.7 | −9.0 | 10.0 | 4.30 | 15.5 | 7.7 | −9.0 | 11.0 | 5.30 | 15.5 | 7.7 | −9.0 | 12.0 | 6.30 | 15.5 | 7.7 |
| −9.0 | 9.0 | 3.40 | 14.8 | 7.2 | −9.0 | 10.0 | 4.40 | 14.8 | 7.2 | −9.0 | 11.0 | 5.40 | 14.8 | 7.2 | −9.0 | 12.0 | 6.40 | 14.8 | 7.2 |
| −10.0 | 9.0 | 1.90 | 24.5 | 12.3 | −10.0 | 10.0 | 2.90 | 24.5 | 12.3 | −10.0 | 11.0 | 3.90 | 24.5 | 12.3 | −10.0 | 12.0 | 4.90 | 24.5 | 12.3 |
| −10.0 | 9.0 | 2.00 | 23.3 | 11.5 | −10.0 | 10.0 | 3.00 | 23.3 | 11.5 | −10.0 | 11.0 | 4.00 | 23.3 | 11.5 | −10.0 | 12.0 | 5.00 | 23.3 | 11.5 |
| −10.0 | 9.0 | 2.10 | 22.3 | 10.8 | −10.0 | 10.0 | 3.10 | 22.3 | 10.8 | −10.0 | 11.0 | 4.10 | 22.3 | 10.8 | −10.0 | 12.0 | 5.10 | 22.3 | 10.8 |
| −10.0 | 9.0 | 2.20 | 21.3 | 10.1 | −10.0 | 10.0 | 3.20 | 21.3 | 10.1 | −10.0 | 11.0 | 4.20 | 21.3 | 10.1 | −10.0 | 12.0 | 5.20 | 21.3 | 10.1 |
| −10.0 | 9.0 | 2.30 | 20.3 | 9.5 | −10.0 | 10.0 | 3.30 | 20.3 | 9.5 | −10.0 | 11.0 | 4.30 | 20.3 | 9.5 | −10.0 | 12.0 | 5.30 | 20.3 | 9.5 |
| −10.0 | 9.0 | 2.40 | 19.4 | 8.9 | −10.0 | 10.0 | 3.40 | 19.4 | 8.9 | −10.0 | 11.0 | 4.40 | 19.4 | 8.9 | −10.0 | 12.0 | 5.40 | 19.4 | 8.9 |
| −10.0 | 9.0 | 2.50 | 18.6 | 8.4 | −10.0 | 10.0 | 3.50 | 18.6 | 8.4 | −10.0 | 11.0 | 4.50 | 18.6 | 8.4 | −10.0 | 12.0 | 5.50 | 18.6 | 8.4 |
| −10.0 | 9.0 | 2.60 | 17.8 | 7.9 | −10.0 | 10.0 | 3.60 | 17.8 | 7.9 | −10.0 | 11.0 | 4.60 | 17.8 | 7.9 | −10.0 | 12.0 | 5.60 | 17.8 | 7.9 |
| −10.0 | 9.0 | 2.70 | 17.0 | 7.5 | −10.0 | 10.0 | 3.70 | 17.0 | 7.5 | −10.0 | 11.0 | 4.70 | 17.0 | 7.5 | −10.0 | 12.0 | 5.70 | 17.0 | 7.5 |
| −10.0 | 9.0 | 2.80 | 16.3 | 7.1 | −10.0 | 10.0 | 3.80 | 16.3 | 7.1 | −10.0 | 11.0 | 4.80 | 16.3 | 7.1 | −10.0 | 12.0 | 5.80 | 16.3 | 7.1 |
| −10.0 | 9.0 | 2.90 | 15.6 | 6.7 | −10.0 | 10.0 | 3.90 | 15.6 | 6.7 | −10.0 | 11.0 | 4.90 | 15.6 | 6.7 | −10.0 | 12.0 | 5.90 | 15.6 | 6.7 |
| −10.0 | 9.0 | 3.00 | 15.0 | 6.4 | −10.0 | 10.0 | 4.00 | 15.0 | 6.4 | −10.0 | 11.0 | 5.00 | 15.0 | 6.4 | −10.0 | 12.0 | 6.00 | 15.0 | 6.4 |
| −11.0 | 9.0 | 1.40 | 24.6 | 10.8 | −11.0 | 10.0 | 2.40 | 24.6 | 10.8 | −11.0 | 11.0 | 3.40 | 24.6 | 10.8 | −11.0 | 12.0 | 4.40 | 24.6 | 10.8 |
| −11.0 | 9.0 | 1.50 | 23.6 | 10.2 | −11.0 | 10.0 | 2.50 | 23.6 | 10.2 | −11.0 | 11.0 | 3.50 | 23.6 | 10.2 | −11.0 | 12.0 | 4.50 | 23.6 | 10.2 |
| −11.0 | 9.0 | 1.60 | 22.8 | 9.6 | −11.0 | 10.0 | 2.60 | 22.8 | 9.6 | −11.0 | 11.0 | 3.60 | 22.8 | 9.6 | −11.0 | 12.0 | 4.60 | 22.8 | 9.6 |
| −11.0 | 9.0 | 1.70 | 21.7 | 9.1 | −11.0 | 10.0 | 2.70 | 21.7 | 9.1 | −11.0 | 11.0 | 3.70 | 21.7 | 9.1 | −11.0 | 12.0 | 4.70 | 21.7 | 9.1 |
| −11.0 | 9.0 | 1.80 | 20.8 | 8.6 | −11.0 | 10.0 | 2.80 | 20.8 | 8.6 | −11.0 | 11.0 | 3.80 | 20.8 | 8.6 | −11.0 | 12.0 | 4.80 | 20.8 | 8.6 |
| −11.0 | 9.0 | 1.90 | 20.0 | 8.2 | −11.0 | 10.0 | 2.90 | 20.0 | 8.2 | −11.0 | 11.0 | 3.90 | 20.0 | 8.2 | −11.0 | 12.0 | 4.90 | 20.0 | 8.2 |
| −11.0 | 9.0 | 2.00 | 19.3 | 7.8 | −11.0 | 10.0 | 3.00 | 19.3 | 7.8 | −11.0 | 11.0 | 4.00 | 19.3 | 7.8 | −11.0 | 12.0 | 5.00 | 19.3 | 7.8 |
| −11.0 | 9.0 | 2.10 | 18.5 | 7.4 | −11.0 | 10.0 | 3.10 | 18.5 | 7.4 | −11.0 | 11.0 | 4.10 | 18.5 | 7.4 | −11.0 | 12.0 | 5.10 | 18.5 | 7.4 |
| −11.0 | 9.0 | 2.20 | 17.8 | 7.0 | −11.0 | 10.0 | 3.20 | 17.8 | 7.0 | −11.0 | 11.0 | 4.20 | 17.8 | 7.0 | −11.0 | 12.0 | 5.20 | 17.8 | 7.0 |
| −11.0 | 9.0 | 2.30 | 17.1 | 6.7 | −11.0 | 10.0 | 3.30 | 17.1 | 6.7 | −11.0 | 11.0 | 4.30 | 17.1 | 6.7 | −11.0 | 12.0 | 5.30 | 17.1 | 6.7 |
| −11.0 | 9.0 | 2.40 | 16.5 | 6.4 | −11.0 | 10.0 | 3.40 | 16.5 | 6.4 | −11.0 | 11.0 | 4.40 | 16.5 | 6.4 | −11.0 | 12.0 | 5.40 | 16.5 | 6.4 |
| −11.0 | 9.0 | 2.50 | 15.9 | 6.1 | −11.0 | 10.0 | 3.50 | 15.9 | 6.1 | −11.0 | 11.0 | 4.50 | 15.9 | 6.1 | −11.0 | 12.0 | 5.50 | 15.9 | 6.1 |
| −11.0 | 9.0 | 2.60 | 15.3 | 5.8 | −11.0 | 10.0 | 3.60 | 15.3 | 5.8 | −11.0 | 11.0 | 4.60 | 15.3 | 5.8 | −11.0 | 12.0 | 5.60 | 15.3 | 5.8 |
| −11.0 | 9.0 | 2.70 | 14.7 | 5.6 | −11.0 | 10.0 | 3.70 | 14.7 | 5.6 | −11.0 | 11.0 | 4.70 | 14.7 | 5.6 | −11.0 | 12.0 | 5.70 | 14.7 | 5.6 |

Having thus disclosed preferred embodiments of the invention, what is claimed is:

1. A lens system for implant into the capsular bag behind the cornea of the human eye after removal of the natural crystalline lens; the lens system comprising:

a positive lens and a negative lens; said lenses in spaced adjustable relation to one another, and being dimensioned for insertion into said capsular bag with the positive lens closer to the cornea than the negative lens, said lenses being interconnected so that each lies on a common optical axis;

at least one haptic member connected to each said lens, the distance between said haptic members being controlled by the ciliary muscles of the human eye and controlling the distance between said lenses; and wherein the spacing between said lenses is inversely proportional to the spacing between said haptic members.

2. The lens system recited in claim 1, wherein said positive lens has a focal length between 5 mm and 12 mm and said negative lens has a focal length between −5 mm and −12 mm.

3. A lens system for implant into the human eye in place of the natural crystalline lens, the lens system comprising:

a convex lens and a concave lens; said lenses in spaced, adjustable relation to one another;

wherein said convex lens is dimensioned to be closer to said cornea than said concave lens;

wherein said lenses are interconnected so that each lies on a common optical axis;

at least one haptic member connected to each said lens, the distance between said haptic members being controlled by the ciliary muscles of the human eye and controlling the distance between said lenses; and wherein the spacing between said lenses is inversely proportional to the spacing between said haptic members.

4. The lens system recited in claim 3 wherein said convex lens has a focal length between 5 mm and 12 mm and said concave lens has a focal length between −5 mm and −12 mm.

5. The lens system recited in claim 3 wherein said lenses are separated by a pressure enclosed chamber.

6. The lens system recited in claim 5 wherein increasing the pressure within said chamber increases the spacing between said lenses.

7. The lens system recited in claim 5 wherein said chamber contains a fluid.

* * * * *